United States Patent
Gerusz et al.

(10) Patent No.: US 6,664,295 B2
(45) Date of Patent: Dec. 16, 2003

(54) FUNGICIDAL PHENYLAMIDINE DERIVATIVES

(75) Inventors: Vincent Gerusz, Lyons (FR); Darren James Mansfield, Lyons (FR); Joseph Perez, Lyons (FR); Jean-Pierre Vors, Lyons (FR); Derek Baldwin, Cambridgeshire (GB); Thomas Lawley Hough, Cambridge (GB); Robert Dale Mitchell, Essex (GB)

(73) Assignee: Bayer CropScience SA (FR)

( * ) Notice: Subject to any disclaimer, the term of this patent is extended or adjusted under 35 U.S.C. 154(b) by 0 days.

(21) Appl. No.: 09/923,146

(22) Filed: Aug. 6, 2001

(65) Prior Publication Data

US 2002/0082267 A1 Jun. 27, 2002

(30) Foreign Application Priority Data

Aug. 4, 2000 (EP) .............................................. 00116844

(51) Int. Cl.$^7$ ........................ A01N 33/02; A01N 33/10; C07C 251/06
(52) U.S. Cl. ........................ 514/637; 564/244; 564/245; 564/247
(58) Field of Search ................................ 564/244, 245, 564/247; 514/637

(56) References Cited

U.S. PATENT DOCUMENTS

| | | | |
|---|---|---|---|
| 3,127,269 A | 3/1964 | Greenhalgh et al. | ............ 96/55 |
| 4,006,243 A | 2/1977 | Strehlke et al. | ............. 424/273 |

FOREIGN PATENT DOCUMENTS

| | | |
|---|---|---|
| DE | 19532345 A1 | 8/1996 |
| DE | 19541146 A1 | 4/1997 |

OTHER PUBLICATIONS

Petroske et al., Chemical Abstracts, vol. 123:278702, 1995.*
Sugizaki et al., Chemical Abstracts, vol. 118:163276, 1993.*
Igura et al., Chemical Abstracts, vol. 106:115269, 1987.*
"Novel Compounds Possessing Potent cAMP and cGMP Phosphodiesterase Inhibitory Activity. Synthesis and Cardiovascular Effects of a Series of Imidazo[1,2–a]quinoxalinones and Imidazo[1,5–a]quinoxalinones and Their Aza Analogues"; D. Davey, et al.; *J. Med. Chem.*; 1991, 34, pp. 2671–2677.
"Preparation of Substituted N–Phenyl–4–aryl– 2–pyrimidinamines as Mediator Release Inhibitors"; R. Paul, et al.; *J. Med. Chem.*; 1993, 36, pp. 2716–2725.
"Imidazole and Benzimidazole Addition to Quinones. Formation of meso and d,l Isomers and Crystal Structure of the d, Isomer of 2,3–Bis(benzimidazol–1'–yl)–1,4–Dihydroxybenzene"; C. Escolastico, et al.; *Tetrahedron*; vol. 50, No. 43, pp. 12489–12510, 1994.

"8–lH–Imidazol–1–yl)–7–nitro–4(5H)–imidazo[1,2–α]quinoxalinone and Related Compounds: Synthesis and Structure–Activity Relationships for the AMPA–type Non–NMDA Receptor"; J. Ohmori, et al.; *J. Med. Chem.*; 1997, 40, pp. 2053–2063.
"(Imidazolylphenyl)pyrrol–2–one Inhibitors of Cardiac cAMP Phosphodiesterase"; J. Lampe, et al.; *J. Med. Chem.*; 1993, 36, pp. 1041–1047.
"Nonsymmetric P2/P2' Cyclic Urea HIV Protease Inhibitors. Structure–Activity Relationship, Bioavailability, and Resistance Profile of Monoindazole–Substituted P2 Analogues"; G. V. DeLucca, et al.; *J. Med. Chem.*; 1998, 41, pp. 2411–2423.
"Irreversible Enzyme Inhibitors. CLXXV. Irreversible Inhibition of Purified Dihydrofolic Reductase"; B.R. Baker, et al.; *Journal of Medicinal Chemistry*; 1970; vol. 15, No. 6; pp. 1143–1148.
"Cardiotonic Agents. 2. (Imidazolyl)aroylimidazolones, Highly Potent and Selective Positive Inotropic Agents"; A. A. Hagedorn, III, et al.; *Med. Chem.*; 1987, 30; pp. 1342–1347.
"Unusual Cleavage of Phenacyl–Substituted Benzimidazolium Salts, Synthesis of 1,4–Diabylimidazoles"; T. A. Kuz menko, et al.; Translated from Khimiya Geterotsillicheskikh Soedinenii; No. 3; Mar. 1982; pp. 388–392.

* cited by examiner

Primary Examiner—Richard L. Raymond
(74) Attorney, Agent, or Firm—Ostrolenk Faber Gerb & Soffen, LLP

(57) ABSTRACT

The invention provides fungicidal compounds of formula I and salts thereof:

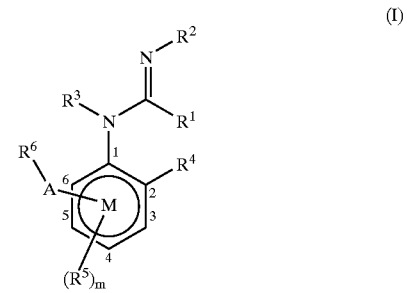

(I)

wherein
 the various radicals and substituents are as defined in the description,
 fungicidal compositions containing them and method for combating fungi which comprises applying these.

24 Claims, No Drawings

FUNGICIDAL PHENYLAMIDINE DERIVATIVES

This invention relates to new fungicidal phenylamidine derivatives, their process of preparation and the fungicidal compositions containing them.

WO 95/22532 relates to substituted phenyltriazolinones claimed as herbicides and discloses inter alia a compound of formula A for which there is no characterising data therein.

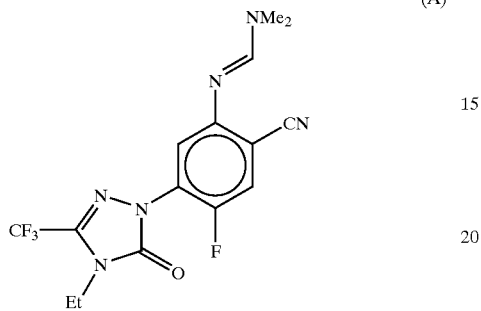

(A)

The abstract, composition claim and use claim refer only to the use of such compounds as herbicides and indeed the description supports the invention only with herbicidal activity data. There is a sentence in the specification that states that certain compounds show fungicidal activity, although no fungicidal activity data are provided. No indication is given as to which compounds are fungicidal and there is no suggestion that compound A could be fungicidal.

We have now found that certain phenylamidines have fungicidal activity. Therefore, the invention provides the use of a compound of general formula (I) and salts thereof as fungicides:

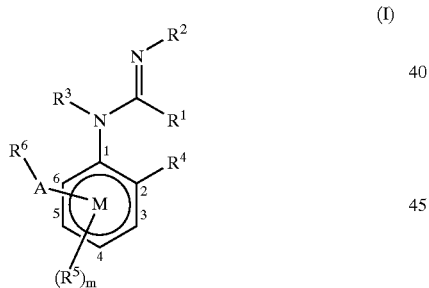

(I)

wherein $R^1$ is chosen from among alkyl, alkenyl, alkynyl, acyl, carbocyclyl, heterocyclyl, each of which may be substituted, cyano and hydrogen;

$R^2$ and $R^3$, which may be the same or different, are any group defined for $R^1$; cyano; acyl; —$OR^a$, —$NR^aR^b$ or —$SR^a$, where $R^a$ and $R^b$, which may be the same or different, are chosen from alkyl, alkenyl, alkynyl, acyl, carbocyclyl, heterocyclyl, each of which may be substituted, and cyano; or $R^2$ and $R^3$, or $R^2$ and $R^1$, together with their interconnecting atoms may form a ring, which may be substituted;

$R^4$ is chosen from among alkyl, alkenyl, alkynyl, carbocyclyl, heterocyclyl, each of which may be substituted; hydroxy; mercapto; azido; nitro; halogen; cyano; acyl; optionally substituted amino; cyanato; thiocyanato; —$SF_5$; —$OR^a$; —$SR^a$ and —$Si(R^a)_3$, where $R^a$ is alkyl, alkenyl, alkynyl, carbocyclyl or heterocyclyl, each of which may be substituted;

m is 0 to 3;

when present $R^5$, which may be the same or different to any other $R^5$, is any group defined for $R^4$;

$R^6$ is optionally substituted carbo- or hetero-cyclyl; and

A is a direct bond, —O—, —$S(O)_n$—, —$NR^9$—, —$CR^7$=$CR^7$—, —C≡C—, —$A^1$—, —$A^1$—$A^1$—, —O—$(A^1)_k$—O—, —O—$(A^1)_k$—, —$A^3$—, —$A^4$—, —$A^1$O—, —$A^1S(O)_n$—, —$A^2$—, —$OA^2$—, —$NR^9A^2$—, —$OA^2$—$A^1$—, —$OA^2$—C($R^7$)=C($R^8$)—, —$S(O)_nA^1$—, —$A^1$—$A^4$—, —$A^1$—$A^4$—C($R^8$)=N—N=$CR^8$—, —$A^1$—$A^4$—C($R^8$)=N—$X^2$—$X^3$—, —$A^1$—$A^4$—$A^3$—, —$A^1$—$A^4$—N($R^9$)—, —$A^1$—$A^4$—X—$CH_2$—, $A^1$—$A^4$—$A^1$—, —$A^1$—$A^4$—$CH_2X$—, —$A^1$—$A^4$—C($R^8$)=N—$X^2$—$X^3$—$X^1$—, —$A^1$—X—C($R^8$)=N—, —$A^1$—X—C($R^8$)=N—N=$CR^8$—, —$A^1$—X—C($R^8$)=N—N($R^9$)—, —$A^1$—X—$A^2$—$X^1$—, —$A^1$—O—$A^3$—, —$A^1$—O—C($R^7$)=C($R^8$)—, —$A^1$—O—N($R^9$)—$A^2$—N($R^9$)—, —$A^1$—O—N($R^9$)—$A^2$—, —$A^1$—N($R^9$)—$A^2$—N($R^9$)—, —$A^1$—N($R^9$)—$A^2$—, —$A^1$—N($R^9$)—N=C($R^8$)—, —$A^3$—$A^1$—, —$A^4$—$A^3$—, —$A^2$—$NR^9$—, —$A^1$—$A^2$—$X^1$—, —$A^1$—$A^1$—$A^2$—$X^1$—, —O—$A^2$—N($R^9$)—$A^2$—, —$CR^7$=$CR^7$—$A^2$—$X^1$—, —C≡C—$A^2$—$X^1$—, —N=C($R^8$)—$A^2$—$X^1$—, —C($R^8$)=N—N=C($R^8$)—, —C($R^8$)=N—N($R^9$)—, —($CH_2$)$_2$—O—N=C($R^8$)—ou—X—$A^2$—N($R^9$)— where:

n is 0, 1 or 2, k is 1 to 9, $A^1$ is —$CHR^7$—, $A^2$ is —C(=X)—, $A^3$ is —C($R^8$)=N—O—, $A^4$ is —O—N=C($R^8$)—,

X is O or S, $X^1$ is O, S, $NR^9$ or a direct bond, $X^2$ is O, $NR^9$ or a direct bond, $X^3$ is hydrogen, —C(=O)—, —$SO_2$— or a direct bond, $R^7$, which may be the same or different to any other $R^7$, is alkyl, alkenyl, alkynyl, cyano, acyl, hydroxy, alkoxy, haloalkoxy, alkylthio, cycloalkyl or phenyl, each of which may be substituted; or is hydrogen or halogen;

$R^8$, which may be the same or different to any other $R^8$, is alkyl, alkenyl, alkynyl, alkoxy, alkylthio, carbo- or hetero-cyclyl, each of which may be substituted; or is hydrogen;

$R^9$, which may be the same or different to any other $R^9$, is optionally substituted alkyl, optionally substituted carbo- or hetero-cyclyl, hydrogen or acyl; or two $R^9$ groups on A, together with the connecting atoms, form a 5 to 7 membered ring;

where the moiety depicted on the right side of linkage A is attached to $R^6$;

or —A—$R^6$ and $R^5$ together with benzene ring M form an optionally substituted fused ring system.

Preferably $R^1$ is alkyl, alkenyl, alkynyl or acyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen), or is cyano or hydrogen. $R^1$ is especially $C_1$–$C_{10}$ alkyl (e.g. methyl) or hydrogen.

Preferably $R^2$ and $R^3$, which may be the same or different, are alkyl, alkenyl or alkynyl, each of which may be substituted by alkoxy, haloalkoxy, alkylthio, halogen or optionally substituted phenyl (preferably phenyl, optionally substituted by alkyl, haloalkyl, alkoxy, haloalkoxy or alkylthio, each containing 1 to 5 carbon atoms, or by halogen), or is hydrogen or alkycarbonyl. $R^2$ and $R^3$, which may be the same or different, are especially $C_1$–$C_{10}$ alkyl (e.g. methyl or ethyl) or hydrogen.

Preferably $R^4$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen); or is hydroxy; halogen; cyano; acyl (preferably —C(=O)$R^c$, —C(=S)$R^c$ or —S(O)$_p R^c$, where $R^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio; phenyloxy, phenylthio, carbocyclyl, heterocyclyl); alkoxy; haloalkoxy; or alkylthio. $R^4$ is especially $C_1$–$C_{10}$ alkyl (e.g. methyl or ethyl) or halogen.

Preferably m is 0 or 1, especially 1.

When present, $R^5$ is preferably a group defined for preferred $R^4$ above. $R^5$ is especially $C_1$–$C_{10}$ alkyl or halogen.

When present, the group $R^5$ is preferably attached at the 5 position of ring M.

Preferably A is a direct bond, —O—, —S(O)$_n A^1$—, —O($A^1$)$_k$—, —S(O)$_n$—, —NR$^9 A^2$—, —$A^2$—, —O$A^2$—, —O$A^2$—$A^1$—, —NR$^9$— or —O($A^1$)$_k$O—. Particularly A is a direct bond, —O—, —S—, —NR$^9$—, —CHR$^7$— or —O—CHR$^7$—. Especially A is a direct bond or —O—.

When present, $R^9$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen); or is hydrogen ($R^9$ is especially $C_1$–$C_{10}$ alkyl or hydrogen).

When present, $R^7$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or by halogen); or is hydroxy; halogen; cyano; acyl; alkoxy; haloalkoxy; alkylthio; or hydrogen ($R^7$ is especially $C_1$–$C_{10}$ alkyl or hydrogen).

Preferably A is attached to the 4 position of benzene ring M.

Preferably $R^6$ is optionally substituted phenyl or optionally substituted aromatic heterocyclyl [preferably thiazolyl, isothiazolyl, thiadiazolyl (particularly 1,2,4-thiadiazolyl), pyridyl or pyrimidinyl].

When substituted, $R^6$ may be substituted by one or more substituents, which may be the same or different, and may be selected from the preferred list: alkyl, alkenyl, alkynyl, carbo- or heterocyclyl, each of which may be substituted; hydroxy; mercapto; azido; nitro; halogen; cyano; acyl; optionally substituted amino; cyanato; thiocyanato; —SF$_5$; —O$R^a$; —S$R^a$ and —Si($R^a$)$_3$, where $R^a$ is alkyl, alkenyl, alkynyl, carbocyclyl or heterocyclyl, each of which may be substituted.

A preferred list of substituents on $R^6$ is: hydroxy; halogen; cyano; acyl (preferably —C(=O)$R^c$, —C(=S)$R^c$ or —S(O)$_p R^c$, where $R^c$ is alkyl, haloalkyl, alkoxy, haloalkoxy, alkylthio, amino, monalkylamino, dialkylamino or phenyl optionally substituted by alkyl, haloalkyl, alkoxy, haloalkoxy or alkylthio, phenyloxy, phenylthio, carbocyclyl, heterocyclyl); amino; alkylamino; dialkylamino; alkyl; haloalkyl; R$^a$O-alkyl; acyloxyalkyl; cyano-oxyalkyl; alkoxy; haloalkoxy; alkylthio;

carbocyclyl (preferably cyclohexyl or cyclopentyl) optionally substituted by alkyl, haloalkyl, alkoxy, haloalkoxy or alkylthio; and benzyl optionally substituted by alkyl, haloalkyl, alkoxy, haloalkoxy or alkylthio.

In a preferred embodiment, the invention provides the use of a compound of general formula (I) and salts thereof as fungicides wherein:

$R^1$ is alkyl, alkenyl or alkynyl, each of which may be substituted by alkoxy, haloalkoxy, alkylthio, halogen or phenyl optionally substituted by alkyl, haloalkyl, alkoxy, haloalkoxy, alkylthio or halogen; or is hydrogen;

$R^2$ and $R^3$, which may be the same or different, are as defined for $R^1$ in this embodiment, or are alkoxy, alkoxyalkoxy, benzyloxy, cyano or alkylcarbonyl;

$R^4$ is alkyl, alkenyl or alkynyl, each of which may be substituted by alkoxy, haloalkoxy, alkylthio, halogen or phenyl optionally substituted by alkyl, haloalkyl, alkoxy, haloalkoxy, alkylthio or halogen; or is hydroxy; halogen; cyano; acyl (preferably —C(=O)$R^c$, —C(=S)$R^c$ or —S(O)$_p R^c$, where $R^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio; phenyloxy, phenylthio, carbocyclyl, heterocyclyl);

m is 0 or 1;

when present, $R^5$ is a group defined for $R^4$ in this embodiment;

A is a direct bond, —O—, —S—, —NR$^9$—, —CHR$^7$— or —O—CHR$^7$—, wherein when present, $R^9$ is alkyl, alkenyl, or alkynyl, each of which may be substituted by alkoxy, haloalkoxy, alkylthio, halogen or phenyl optionally substituted by alkyl, haloalkyl, alkoxy, haloalkoxy, alkylthio, or halogen; or is hydrogen; and $R^7$ is a group defined for $R^9$ in this embodiment, or is hydroxy; halogen; cyano; acyl; alkoxy; haloalkoxy or alkylthio;

A is attached to the 4 position of benzene ring M; and $R^6$ is phenyl or aromatic heterocyclyl, optionally substituted by one or more substituents, which may be the same or different, and may be selected from the list: hydroxy; halogen; cyano; acyl (preferably —C(=O)$R^c$, —C(=S)$R^c$ or —S(O)$_p R^c$, where $R^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio; or phenyloxy, phenylthio, carbocyclyl, heterocyclyl); amino; alkylamino; dialkylamino; alkyl; haloalkyl; R$^a$O-alkyl; acyloxyalkyl; cyano-oxyalkyl; alkoxy; haloalkoxy; alkylthio; carbocyclyl (preferably cyclohexyl or cyclopentyl) optionally substituted by alkyl, haloalkyl, alkoxy, haloalkoxy or alkylthio; and benzyl optionally substituted by alkyl, haloalkyl, alkoxy, haloalkoxy or alkylthio.

Any alkyl group may be straight or branched and is preferably of 1 to 10 carbon atoms, especially 1 to 7 and particularly 1 to 5 carbon atoms.

Any alkenyl or alkynyl group may be straight or branched and is preferably of 2 to 7 carbon atoms and may contain up to 3 double or triple bonds which may be conjugated, for example vinyl, allyl, butadienyl or propargyl.

Any carbocyclyl group may be saturated, unsaturated or aromatic, and contain 3 to 8 ring-atoms. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Any heterocyclyl group may be saturated, unsaturated or aromatic, and contain 3 to 7 ring-atoms up to 4 of which may be hetero-atoms such as nitrogen, oxygen and sulphur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl (and pyridyl N-oxide), piperidinyl, dioxanyl, morpholino, dithianyl, thiomorpholino, pyridazinyl, pyrimidinyl, pyrazinyl, piperazinyl, sulpholanyl, tetrazolyl, triazinyl, azepinyl, oxazepinyl, thiazepinyl, diazepinyl and thiazolinyl.

In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Any alkyl, alkenyl, alkynyl, carbocyclyl or heterocyclyl group, when substituted, may be substituted by one or more substituents, which may be the same or different, and may be selected from the list: hydroxy; mercapto; azido; nitro; halogen; cyano; acyl; alkoxycarbonyl; optionally substituted aminocarbonyl; optionally substituted amino; optionally substituted ammonio; optionally substituted carbocyclyl; optionally substituted heterocyclyl; cyanato; thiocyanato; —SF$_5$; —OR$^a$; —SR$^a$; —SOR$^a$; —SO$_2$R$^a$ and —Si(R$^a$)$_3$, where R$^a$ is alkyl, alkenyl, alkynyl, carbocyclyl or heterocyclyl, each of which may be substituted. In the case of any carbocyclyl or heterocyclyl group the list includes additionally: alkyl, alkenyl and alkynyl, each of which may be substituted. Preferred substituents on any alkyl, alkenyl or alkynyl group are alkoxy, haloalkoxy or alkylthio, each containing 1 to 5 carbon atoms; halogen; or optionally substituted phenyl. Preferred substituents on any carbocyclyl or heterocyclyl group are alkyl, haloalkyl, alkoxy, haloalkoxy or alkylthio, each containing 1 to 5 carbon atoms; halogen; or optionally substituted phenyl.

In the case of any alkyl group or any unsaturated ring-carbon in any carbocyclyl or heterocyclyl group the list includes a divalent group such as oxo or imino, which may be substituted by optionally substituted amino, R$^a$ or —OR$^a$ (where R$^a$ is as defined above). Preferred groups are oxo, imino, alkylimino, oximino, alkyloximino or hydrazono.

Any amino group, when substituted and where appropriate, may be substituted by one or two substituents which may be the same or different, selected from the list: optionally substituted alkyl, alkenyl, alkynyl, carbocyclyl, or heterocyclyl, optionally substituted amino, —OR$^a$ (where R$^a$ is as defined above) and acyl groups. Alternatively two substituents together with the nitrogen to which they are attached may form a heterocyclyl group, preferably a 5 to 7-membered heterocyclyl group, which may be substituted and may contain other hetero atoms, for example morpholino, thiomorpholino or piperidinyl.

The term acyl includes the residues of sulphur and phosphorus-containing acids as well as carboxylic acids. Typically the residues are covered by the general formulae —C(=X$^a$)R$^b$, —S(O)$_p$R$^b$ and —P(=X$^a$)(OR$^a$)(OR$^a$), where appropriate X$^a$ is O or S, R$^b$ is as defined for R$^a$, —OR$^a$, —SR$^a$, optionally substituted amino or acyl; and p is 1 or 2. Preferred groups are —C(=O)R$^c$, —C(=S)R$^c$, and —S(O)$_p$R$^c$ where R$^c$ is alkyl, C$_1$–C$_5$ alkoxy, C$_1$–C$_5$ alkylthio, phenyl, phenyloxy, phenylthio, carbocyclyl, heterocyclyl or amino, each of which may be substituted.

Complexes of compounds of the invention are usually formed from a salt of formula MAn or MAn$_2$, in which M is a metal cation, e.g. copper, manganese, cobalt, nickel, iron or zinc and An is an anion, e.g. chloride, nitrate or sulphate.

In cases where the compounds of the invention comprise a nitrogen atom which may be oxidised, N-oxides of such compounds are also part of the invention.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof In cases where the compounds of the invention exist as optical isomers, the invention includes individual isomers as well as mixtures thereof, including the racemic mixture.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), late tomato or potato blight (*Phytophthora infestans*), apple scab (*Venturia inaequalis*), and glume blotch (*Leptosphaeria nodorum*). Other fungi against which the compounds may be active include other powdery mildews, other rusts, and other general pathogens of Deuteromycete, Ascomycete, Phycomycete and Basidomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal, acaricidal, antimicrobial or antibacterial properties. Alternatively the compound of the invention can be used in a simultaneous, sequential or alternative way with the other active ingredient(s).

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or alkyl phenol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkylnaphthalene sulphonates, e.g. butylnaphthalene sulphonate; salts of sulphonated naphthaleneformaldehyde condensates; salts of sulphonated phenolformaldehyde condensates; or more complex sulphonates such as the amide sulphonates, e.g. the sulphonated condensation product of oleic acid and N-methyl taurine; the dialkyl sulphosuccinates, e.g. the sodium sulphonate of dioctyl succinate; acid derivatives of alkyl glycosides and alkylpolyglycosides materials and their metal salts, e.g. alkyl polyglycoside citrate or tartrate materials; or mono-, di- and tri-alkyl esters of citric acid and their metal salts.

Nonionic agents include condensation products of fatty acid esters, fatty alcohols, fatty acid amides or fatty-alkyl- or alkenyl-substituted phenols with ethylene and/or propylene oxide; fatty esters of polyhydric alcohol ethers, e.g. sorbitan fatty acid esters; condensation products of such esters with ethylene oxide, e.g. polyoxyethylene sorbitan fatty acid esters; alkyl glycosides, alkyl polyglycoside materials; block copolymers of ethylene oxide and propylene oxide; acetylenic glycols such as 2,4,7,9-tetramethyl-5-decyne-4,7-diol, ethoxylated acetylenic glycols; acrylic based graft copolymers; alkoxylated siloxane surfactants; or imidazoline type surfactants, e.g. 1-hydroxyethyl-2-alkylimidazoline.

Examples of a cationic surface-active agent include, for instance, an aliphatic mono-, di-, or polyamine as an acetate, naphthenate or oleate; an oxygen-containing amine such as an amine oxide, polyoxyethylene alkylamine or polyoxypropylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, an aerosol, a dispersion, an aqueous emulsion, a microemulsion, a dispersible concentrate, a dusting powder, a seed dressing, a fumigant, a smoke, a dispersible powder, an emulsifiable concentrate, granules or an impregnated strip. Moreover it can be in a suitable form for direct application or as a concentrate or primary composition which requires dilution with a suitable quantity of water or other diluent before application.

A dispersible concentrate comprises a compound of the invention dissolved in one or more water miscible or semi-water miscible solvents together with one or more surface active and/or polymeric material. Addition of the formulation to water results in the crystalisation of the active ingredient, the process being controlled by the surfactants and/or polymers resulting in a fine dispersion.

A dusting powder comprises a compound of the invention intimately mixed and ground with a solid pulverulent diluent, for example, kaolin.

An emulsifiable concentrate comprises a compound of the invention dissolved in a water-immiscible solvent which forms an emulsion or microemulsion on addition to water in the presence of an emulsifying agent.

A granular solid comprises a compound of the invention associated with similar diluents to those that may be employed in dusting powders, but the mixture is granulated by known methods. Alternatively it comprises the active ingredient absorbed or coated on a preformed granular carrier, for example, Fuller's earth, attapulgite, silica or limestone grit.

Wettable powders, granules or grains usually comprise the active ingredient in admixture with suitable surfactants and an inert powder diluent such as clay or diatomaceous earth.

Another suitable concentrate is a flowable suspension concentrate which is formed by grinding the compound with water or other liquid, surfactants and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 percent by weight of the composition.

In use a compound of the invention is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth, as this is the time when the plant can be most severely damaged. The spray or dust can conveniently contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to harvested fruits, vegetables or seeds to prevent infection during storage.

In addition, the compounds of the invention can be applied to plants or parts thereof which have been genetically modified to exhibit a trait such as fungal and/or herbicidal resistance.

In addition the compounds of the invention can be used to treat fungal infestations in timber and in public health applications. Also the compounds of the invention can be used to treat fungal infestations in domestic and farm animals.

Compounds of the invention may be prepared, in known manner, in a variety of ways.

Compounds of general formula I may be prepared from compounds of general formula II according to Scheme 1. Such reactant can be obtained from commercial suppliers or prepared by methods apparent to the skilled in the art. As a general manner, all starting materials used for the preparation of the compounds of the invention are either commercially available or can be prepared by well-known method from the skilled in the art. Such methods can for example be found in the literature, in patents, in the "Chemical Abstracts", in electronic databases or on the Internet.

Scheme 1

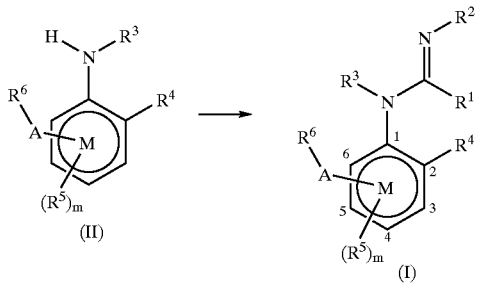

The following reaction conditions may be used to effect conversion:

a) when $R^1$ is hydrogen, by reaction with $H(C=O)NHR^2$ in the presence of $POCl_3$ or $SOCl_2$.

b) reaction with $EtOCH=NR^{10}$ or $EtSCH=NR^{10}$ where $R^{10}$ is a group such as alkyl or —CN.

c) in addition when $R^{10}$ is cyano, compounds of general formula I can be converted into other groups as defined for $R^2$ by heating in the presence of a tertiary amine.

Such reactions are well known from the one skilled in the art and can be conducted for example according general references such as J. March, *Advanced Organic Chemistry*, IV edition, pages 1276 sqq.

Compounds of general formula II may be prepared from compounds of general formula III by removal of a suitable protecting group from nitrogen, for example, the benzyloxycarbonyl group as shown in Scheme 2. Preferred reaction conditions are heating a solution of compound III in 80% dioxan with 20% 2N aqueous HCl. Other standard methods will be apparent to the chemist skilled in the art.

Scheme 2

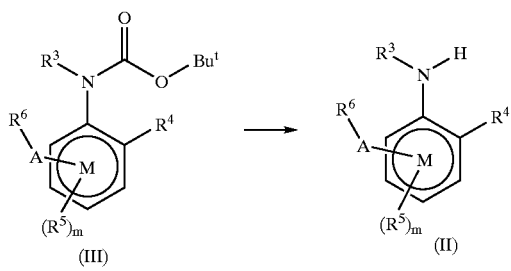

Compounds of general formula III may be prepared from compounds of general formula IV according to Scheme 3. The following reaction conditions may be used to effect this conversion:

a) treatment of compounds of formula IV with a strong base, for example sodium hydride, followed by an alkylating agent, for example R'-Br or R'-I where R' represents alkyl;

b) treatment with an acyl chloride in the presence of a mild base such as pyridine or triethylamine.

Other standard methods will be apparent to the chemist skilled in the art.

Scheme 3

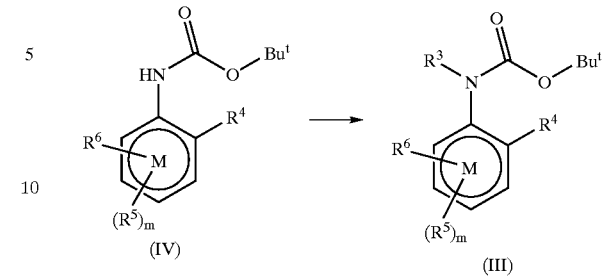

Compounds of general formula IV may be prepared from compounds of general formula V according to Scheme 4. Preferred reaction conditions comprise reaction with ($^tBuOC=O)_2O$ at ambient temperature in alcoholic solvents. Alternative protection groups to $^tBuOC=O$ will be apparent to the chemist skilled in the art for these series of reactions.

Scheme 4

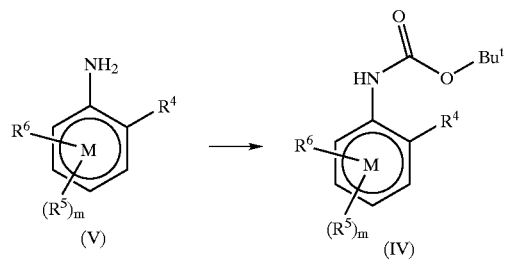

Compounds of general formula V may be prepared by reduction of the nitro group in compounds of formula VI according to reaction Scheme 5. Preferred reaction conditions comprise reaction with stannous chloride in concentrated hydrochloric acid.

Scheme 5

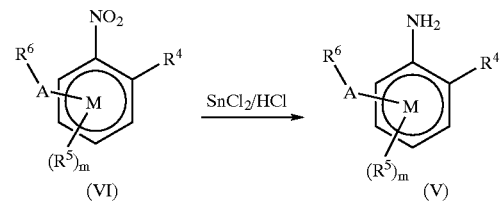

Compounds of formula Va, i.e. compounds of general formula V where A is a direct bond, may be prepared according to reaction Scheme 6, where $X^V$ is a leaving group.

Scheme 6

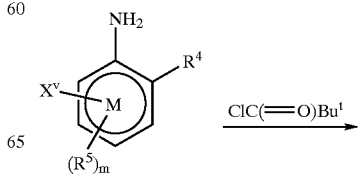

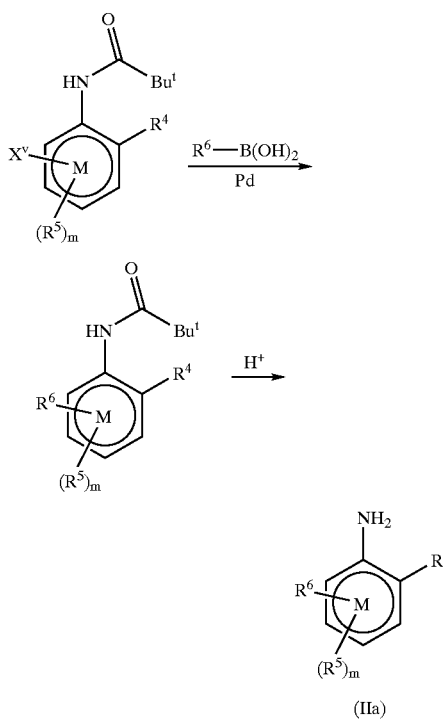

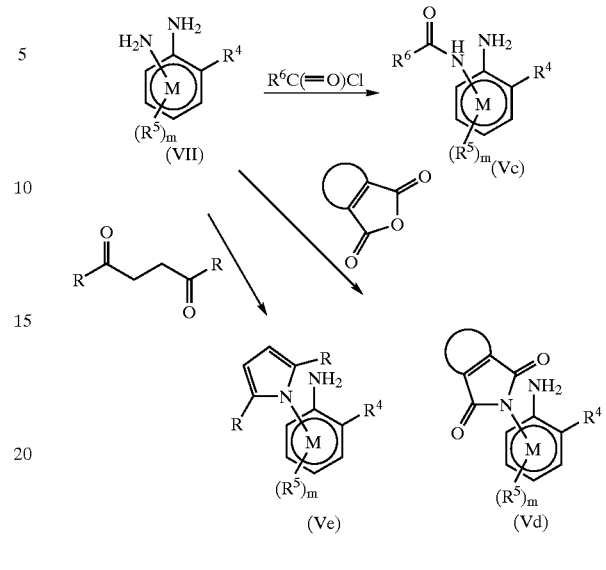

Compounds of formula VIa, i.e. compounds of general formula VI where A is a group $A^Z$, may be prepared by reacting compounds of formula VIII with compounds of formula IX according to reaction Scheme 9. $A^Z$ is a group which, in compound VIII, forms an anion under basic conditions. $A^Z$ is alternatively a basic primary or secondary nitrogen atom. $X^Z$ is a leaving group, preferably halogen. When $A^Z$ is oxygen, preferred reaction conditions comprise treating VIII with sodium hydride followed by addition of IX. When $A^Z$ is sulphur preferred reaction conditions comprise reacting VIII with IX in the presence of a tertiary amine base such as ethyldiisopropylamine. When $A^Z$ is —$CHR^7$—, preferred reaction conditions comprise treating VIII with potassium tert-butoxide in dimethylformamide at low temperature. When $A^Z$ is a basic nitrogen atom, no base is required.

Compounds of formula Vb, i.e. compounds of general formula V where $R^4$ is halogen, may be prepared according to Scheme 7 where $X^T$ represents halogen. When $R^4$ is bromine preferred reaction conditions comprise stirring with bromine in a suitable solvent.

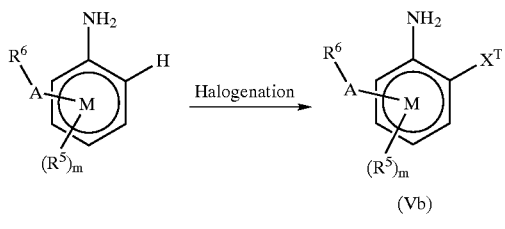

Compounds of formula Vc, i.e. compounds of general formula V where A is NHC(=O)—; compounds of formula Vd, i.e. compounds of formula V where A is a direct bond and $R^6$ is optionally substituted phthalimido, where the curved line connecting the 3 and 4 positions of the phthalimido group represents the optionally substituted carbocyclic ring; and compounds of formula Ve, i.e. compounds of general formula V where A is a direct bond and $R^6$ is pyrrolyl, optionally substituted at the 2 and 5 positions by one or more groups R which may be the same or different; may be prepared from compounds of formula VII according to methodology shown in reaction Scheme 8. For certain compounds of formula VII, protection/deprotection of the amino group ortho to $R^4$ may be required to improve yields.

Scheme 9

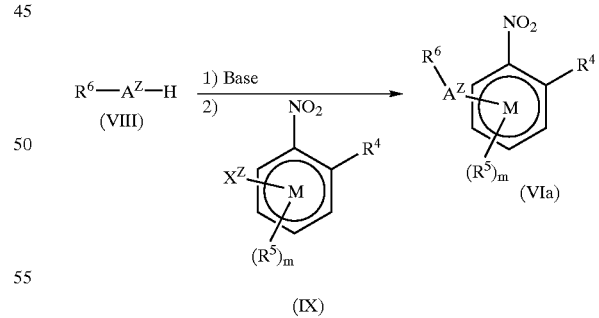

Compounds of formula VIb, i.e. compounds of general formula VI where A is a group $A^W$, may be prepared by reacting compounds of formula X with compounds of formula XI according to reaction scheme 10. $A^W$ is a group which, in compound X, forms an anion under basic conditions. $X^W$ is a leaving group, preferably halogen. Preferred basic conditions comprise reaction of X with potassium carbonate or sodium hydride followed by addition of XI.

Scheme 10

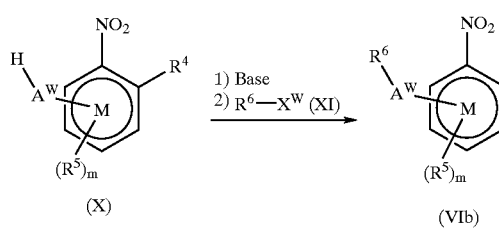

Compounds of formula VIc, i.e. compounds of general formula VI where A is O, may be prepared by reacting compounds of formula XII with boronic acids of formula XIII according to Scheme 11. Preferred reaction conditions comprise reaction with copper acetate and triethylamine.

Scheme 11

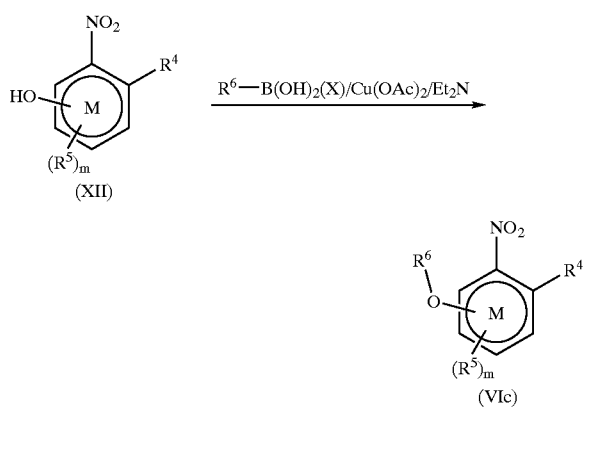

Compounds of formula VId, i.e. compounds of formula VI where A is a direct bond may be prepared according to reaction Scheme 12 from compounds of formula XIV where $X^Z$ is a leaving group, preferably halogen.

Scheme 12

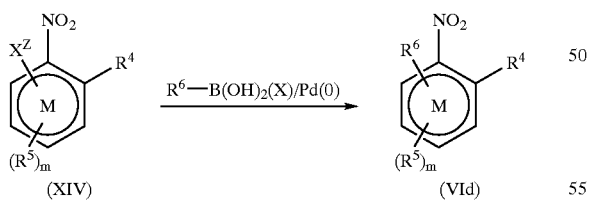

Compounds of formula VI where A is a direct bond and $R^6$ is a heterocyclyl can be prepared using a variety of methods known to a skilled chemist (for example see "Comprehensive Heterocyclic Chemistry", Vols 1–7, A. R. Katritzky and C. W. Rees). By way of example, routes to compounds of formula VI containing a 1,2,4-oxadiazol-3-yl group (compound VIe) and a 1,3,4-oxadiazol-2-yl group (compound VIf) are shown in Schemes 13 and 14.

Scheme 13

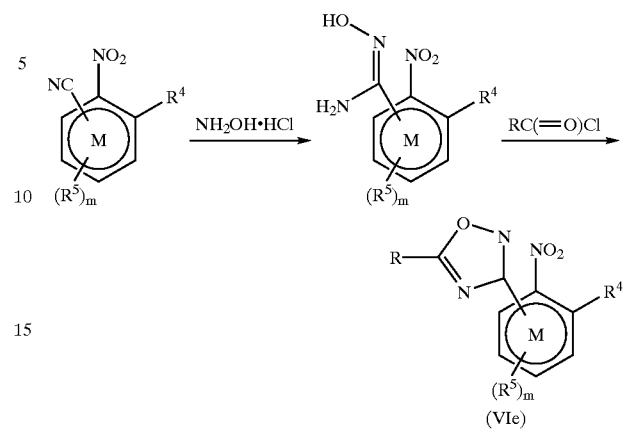

Scheme 14

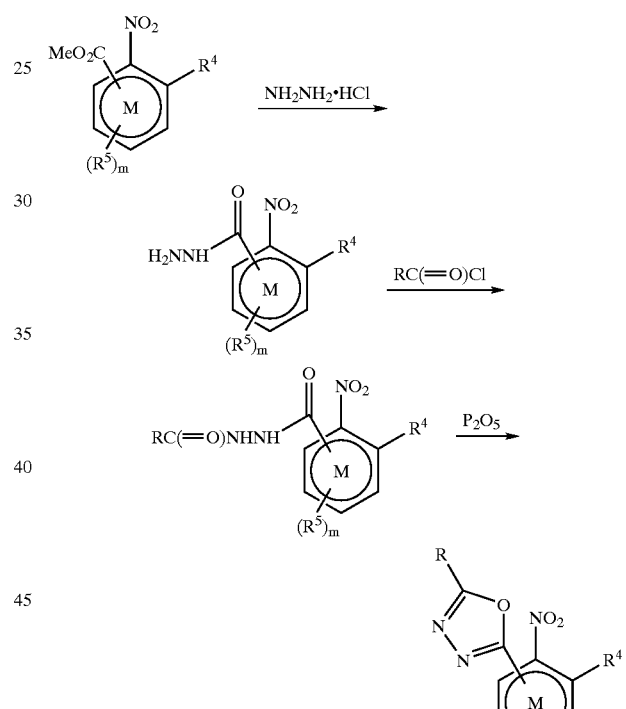

Other methods will be apparent to the chemist skilled in the art, as will be methods for preparing starting materials and intermediates.

In addition, compounds of the invention may be prepared using combinatorial chemistry methodology.

The invention is illustrated in the following Examples. Structures of isolated, novel compounds were confirmed by N.M.R., mass spectrometry and/or other appropriate analyses. Proton N.M.R. spectra ($^1$H N.M.R.) were determined in deuterochloroform and chemical shifts (δ) are quoted in parts per million downfield of tetramethylsilane.

EXAMPLE 1

Preparation of N-methyl-N'-methyl-[4-(3-tert-butylphenoxy)-2,5-xylyl]formamidine (Compound 2, see Table 1 Below)

To the product from stage a) (1.0 g) and N-methylformamidine (0.25 g) in orthodichlorobenzene (5 ml) was added thionyl chloride (0.46 g). The solution was heated at 65° C. for 3 hours and allowed to cool to ambient temperature. Triethylamine was added, followed by water and the product was extracted into ethyl acetate. The organic phase was washed with sodium hydrogenocarbonate solution and evaporated to dryness. The crude product was purified by flash chromatography to afford the title compound as a pale yellow oil (0.60 g).

Preparation of Starting Materials

Stage a): Preparation of N-methyl-[4-(3-tert-butylphenoxy)-2,5-xylyl]aniline The product from stage b) (4.8 g) was dissolved in dioxan (50 ml) and 2N hydrochloric acid (15 ml), and the solution was heated at reflux for one hour. After cooling the mixture was poured into water and neutralised with 2N sodium hydroxide solution. The product was extracted into ethyl acetate, washed once with water, and concentrated to a brown oil which crystallised on standing to afford the title compound (3.15 g).

Stage b): Preparation of N-methyl-N-tert-butoxycarbonyl-[4-(3-tert-butylphenoxy)-2,5-xylyl]aniline Sodium hydride (0.54 g, 60% in mineral oil) was added to a solution of the product from stage c) (4.7 g) in dimethylformamide (70 ml) at 0°C. and the mixture was stirred at this temperature for one hour. Methyl iodide (1.9 g) was then added dropwise and the solution was stirred for 4 hours.

The reaction mixture was poured into water (500 ml) and extracted with ether. The combined ether extracts were washed once with water, brine, dried over magnesium sulphate, filtered and concentrated to dryness, to afford the title compound (4.85 g) as a brown oil.

Stage c): Preparation of N-tert-butoxycarbonyl-[4-(3-tert-butylphenoxy)-2,5-xylyl]aniline To a solution of the product from stage d) (8.1 g) and triethylamine(4.5 g) in methanol (100 ml) was added dropwise a solution of tert-butoxycarbonyl anhydride (13.7 g) in methanol (20 ml). The solution was stirred at ambient temperature for one hour and evaporated to dryness. Water was added and the product was extracted into ethyl acetate, which was washed once with water, dried over magnesium sulphate, filtered and concentrated to a brown oil. The title compound was purified by flash chromatography to afford a colourless solid (9.0 g)

Stage d): Preparation of 4-(3-tert-butylphenoxy)-2,5-xylidine

To a stirred mixture of stannous chloride (10.8 g) in concentrated hydrochloric acid (24 ml) and ethanol (50 ml) was added the product from stage e) below (2.46 g) and the mixture was heated at 75° C. for 2 hours. On cooling potassium hydroxide solution was added slowly with cooling. The mixture was extracted with diethyl ether (×3) and the combined extracts were washed with brine, dried over magnesium sulphate, filtered and evaporated to dryness to give a crude residue which was purified by silica gel chromatography eluting with light petroleum (b.p.60–80° C.)/ethyl acetate (3:1) to give the title product.

Stage e): Preparation of 2-nitro-5-(3-tert-butylphenoxy)-p-xylene

To a suspension of sodium hydride (0.4 g of 60% in oil) in dry N-methylpyrrolidinone (10 ml) was slowly added 3-tert-butylphenol (1.62 g). When effervescence had ceased, 3-chloro-6-nitro-p-xylene (1.85 g) was added and the mixture stirred at 120–40° C. for 5 hours. On cooling, the mixture was poured into water and the mixture extracted with diethyl ether (×3). The combined ether extracts were dried over magnesium sulphate, filtered and evaporated to give the title compound as a solid.

The following compounds of formula Ia (see Table 1), i.e. compounds of general formula I where —A—R⁶ is para to the amidine moiety, may be prepared by methods analogous to those of Example 1.

TABLE 1

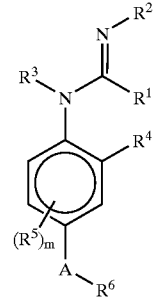

(Ia)

| Cmpd | R1 | R2 | R3 | R4 | R5 | A | R6 |
|---|---|---|---|---|---|---|---|
| 1 | H | CN | Me | Me | 5-Me | O | m-t-Buphenyl |
| 2 | H | Me | Me | Me | 5-Me | O | m-t-Buphenyl |
| 3 | H | Me | n-Propyl | Me | 5-Me | O | m-t-Buphenyl |
| 4 | H | Me | Et | Me | 5-Me | O | m-t-Buphenyl |
| 5 | H | Et | Me | Me | 5-Me | O | m-t-Buphenyl |
| 6 | H | Et | n-Propoyl | Me | 5-Me | O | m-t-Buphenyl |
| 7 | H | CN | Me | Me | 5-Me | O | m-trifluoro-methyl-p-chlorophenyl |
| 8 | H | CN | Et | Me | 5-Me | O | m-trifluoro-methyl-p-chlorophenyl |
| 9 | H | CN | Acetyl | Me | 5-Me | O | m-trifluoro-methyl-p-chlorophenyl |
| 10 | H | 4-fluorobenzyl | Et | Me | 5-Me | O | m-trifluoro-methyl-p-chlorophenyl |

Note:
H = hydrogen; Me = methyl; Et = ethyl; CN = cyano; n = linear; m = meta; t = tertio; p = para.

TABLE 2

Analytical data

| Cmpd | NMR (CDCl$_3$) | MS (M + 1) |
|---|---|---|
| 1 |  | 382 |
| 2 | 1.25(s, 9H, C(CH3)3); 2.10(s, 3H, ArCH3); 2.15(s, 3H, ArCH3); 3.10(s, 3H, N(CH3)); 3.15(s, 3H, N(CH3)) |  |
| 3 | 0.80(t, 3H, CH2CH3); 1.20(s, 9H, C(CH3)3); 1.50(q, 2H, CH2CH2CH3); 2.10(s, 9H, ArCH3); 2.15(s, 3H, ArCH3); 3.10(s, 3H, N(CH3)); 3.50(m, 2H, N(CH2CH2) |  |
| 4 | 1.00(t, 3H, CH2CH3); 1.20(s, 9H, C(CH3)3); 2.10(s, 3H, ArCH3); 2.15(s, 3H, ArCH3); 3.10(s, 3H, NCH3); 3.60(q, 2H, NCH2CH3) |  |
| 5 | 1.10(t, 3H, CH2CH3); 1.25(s, 9H, C(CH3)3); 2.10(s, 3H, ArCH3); 2.15(s, 3H, ArCH3); 3.10(s, 3H, NCH3); 3.30(q, 2H, NCH2) |  |
| 6 | 0.80(t, 3H, CH2CH2CH3); 1.05(t, 3H, CH2CH3); 1.20(s, 9H, C(CH3)3); 1.50(m, 2H, CH2CH2CH3); 2.10(s, 3H, ArCH3); 2.15(s, 3H, ArCH3); 3.20(q, 2H, CH2CH3); 3.40(m, 2H, CH2CH2CH3) |  |
| 8 | 1.2(t, 3H, NCH2CH3); 2.15(s, 3H, ArCH3); 2.2(s, 3H, ArCH3); 3.8(q, 2H, NCH2CH3) |  |
| 9 |  | 336 |
| 10 |  | 479 |

Note:
Proton N.M.R. spectra ($^1$H N.M.R.) were determined in deuterochloroform and chemical shifts (δ) are quoted in parts per million downfield of tetramethylsilane. Mass spectrometry data (MS) were obtained using API + technique.

Test Examples

Compounds were assessed for activity against one or more of the following Phytopathogenic diseases:

*Erysiphe graminis* f. sp. *tritici:* wheat powdery mildew

*Puccinia recondita:* wheat brown rust

*Septoria nodorum:* wheat septoria nodorum

*Septoria tritici:* wheat septoria tritici

*Pyrenophora teres:* barley net blotch

Aqueous solutions or dispersions of the compounds of the invention at the desired concentration, including one or more wetting agents, were applied by spray or by drenching the stem base of the test plants, as appropriate. After a given time, plants or plant parts were inoculated with appropriate test pathogens and kept under controlled environmental conditions suitable for maintaining plant growth and development of the disease. After an appropriate time, the degree of infection of the affected part of the plant was visually estimated. At a concentration of 500 ppm (w/v) or less, the following compounds present a control of at least 65% on the specified fungal diseases versus non-treated test.

| | |
|---|---|
| *Erysiphe graminis f. sp. tritici:* | 5, 10 |
| *Leptosphaeria nodorum:* | 10 |
| *Pyrenophora teres:* | 10 |

What is claimed is:

1. A compound of general formula I or salts thereof as fungicides

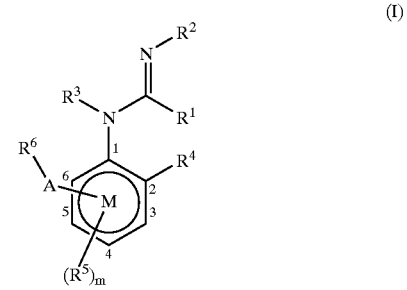

wherein $R^1$ is selected from the group consisting of alkyl, which may be substituted cyano, and hydrogen;

$R^2$ and $R^3$ are independently selected from the group consisting of cyano, acyl, alkyl, and benzyl, each of which may be substituted; or $R^2$ and $R^3$, together with their interconnecting atoms may form a ring, which may be substituted;

$R^4$ and $R^5$ are independently selected from the group consisting of alkyl, which may be substituted, halogen, cyano, acyl, and —OR$^a$ where R$^a$ which may be substituted;

m is 1;

$R^6$ is optionally substituted carbo- or hetero-cyclyl; and

A is a direct bond or —O—.

2. A compound according to claim 1 wherein $R^1$ is alkyl, which may be substituted by alkoxy, haloalkoxy, alkylthio, halogen or optionally substituted phenyl; or is cyano or hydrogen.

3. A compound according to claim 2 wherein $R^1$ is alkyl, which may be substituted by alkoxy, haloalkoxy, alkylthio, halogen or phenyl optionally substituted by alkyl, haloalkyl, alkoxy, haloalkoxy or alkylthio, each containing 1 to 5 carbon atoms, or halogen, or is hydrogen.

4. A compound according to claim 1 wherein $R^1$ is $C_1$–$C_{10}$ alkyl or hydrogen.

5. A compound according to claim 1 wherein $R^1$ is methyl or hydrogen.

6. A compound according to claim 1 wherein $R^2$ and $R^3$, which may be the same or different, are alkyl, which may be substituted by alkoxy, haloalkoxy, alkylthio, halogen or optionally substituted phenyl, or are alkylcarbonyl.

7. A compound according to claim 1 wherein $R^2$ and $R^3$, which may be the same or different, are alkyl, which may be substituted by alkoxy, haloalkoxy, alkylthio, halogen or phenyl optionally substituted by alkyl, haloalkyl, alkoxy, haloalkoxy or alkylthio, each containing 1 to 5 carbon atoms, or by halogen, or are alkylcarbonyl.

8. A compound according to claim 1 wherein $R^2$ and $R^3$, which may be the same or different, are $C_1$–$C_{10}$ alkyl.

9. A compound according to claim 1 wherein $R^2$ and $R^3$ are methyl.

10. A compound according to claim 1 wherein $R^4$ is alkyl, which may be substituted by alkoxy, haloalkoxy, alkylthio, halogen or optionally substituted phenyl; or is halogen; cyano; acyl; or alkoxy.

11. A compound according to claim 1 wherein $R^4$ is alkyl, which may be substituted by alkoxy, haloalkoxy, alkylthio, halogen or phenyl optionally substituted by alkyl, haloalkyl, alkoxy, haloalkoxy or alkylthio, each containing 1 to 5 carbon atoms, or halogen; or is halogen; cyano; acyl; or alkoxy.

12. A compound according to claim 1 wherein $R^4$ is alkyl, which may be substituted by alkoxy, haloalkoxy, alkylthio, halogen or optionally substituted phenyl; or is halogen; cyano; —C(=O)$R^c$, where Rc is alkyl or alkoxy.

13. A compound according to claim 1 wherein $R^4$ is $C_1$–$C_{10}$ alkyl or halogen.

14. A compound according to claim 1 wherein $R^4$ is methyl or ethyl or halogen.

15. A compound according to claim 1 wherein $R^5$ is attached at the 5 position of ring M.

16. A compound according to claim 1 wherein A is attached to the 4 position of benzene ring M.

17. A compound according to claim 1 wherein $R^6$ is optionally substituted aromatic heterocyclyl.

18. A compound according to claim 1 wherein $R^6$ is optionally substituted thiazolyl, isothiazolyl, thiadiazolyl, pyridyl or pyrimidinyl.

19. A compound according to claim 1 wherein $R^6$ is optionally substituted 1,2,4-thiadiazolyl.

20. A compound according to claim 1 wherein $R^6$ may be substituted by one or more substituents, which may be the same or different, and may be selected from the list: alkyl, alkenyl, alkynyl, carbo- or heterocyclyl, each of which may be substituted; hydroxy; mercapto; azido; nitro; halogen; cyano; acyl; optionally substituted amino; cyanato; thiocyanato; —$SF_5$; —$OR^a$; —$SR^a$ and —$Si(R^a)_3$, where $R^a$ is alkyl, alkenyl, alkynyl, carbocyclyl or heterocyclyl, each of which may be substituted.

21. A compound according to claim 1 wherein $R^6$ may be substituted by one or more substituents, which may be the same or different, and may be selected from the list: hydroxy; halogen; cyano; acyl; amino; alkylamino; dialkylamino; alkyl; haloalkyl; RaO-alkyl; acyloxyalkyl; cyanooxyalkyl; alkoxy; haloalkoxy; alkylthio; carbocyclyl, optionally substituted by alkyl, haloalkyl, alkoxy, haloalkoxy or alkylthio; and benzyl optionally substituted by alkyl, haloalkyl, alkoxy, haloalkoxy or alkylthio.

22. A compound according to claim 1 wherein $R^5$ is alkyl, which may be substituted by alkoxy, haloalkoxy, alkylthio, halogen or optionally substituted phenyl; or is halogen; cyano; acyl; or alkoxy.

23. A fungicidal composition comprising at least one compound as claimed in claim 1 in admixture with an agriculturally acceptable diluent or carrier.

24. A method of combating fungi at a locus infested or liable to be infested therewith, which comprises applying to the locus a compound as claimed in claim 1.

* * * * *

UNITED STATES PATENT AND TRADEMARK OFFICE
CERTIFICATE OF CORRECTION

PATENT NO.    : 6,664,295 B2
DATED         : December 16, 2003
INVENTOR(S)   : Gerusz et al.

It is certified that error appears in the above-identified patent and that said Letters Patent is hereby corrected as shown below:

<u>Title page,</u>
Item [75], Inventors, please correct to read as follows:
-- Vincent Gerusz, San Antonio, Texas (US)
   Darren James Mansfield, Lyon (FR)
   Joseph Perez, Lyon (FR)
   Jean-Pierre Vors, Lyon (FR)
   Derek Bladwin, Essex (GB)
   Thomas Lawley Hough, Cambridge (GB)
   Dale Robert Mitchell, Essex (GB) --

Signed and Sealed this

Third Day of May, 2005

JON W. DUDAS
*Director of the United States Patent and Trademark Office*